(12) United States Patent
Götzen

(10) Patent No.: US 7,718,127 B2
(45) Date of Patent: May 18, 2010

(54) MICROFLUIDIC CHIP

(75) Inventor: Reiner Götzen, Duisburg (DE)

(73) Assignee: microTec Gesellschaft für Mikrotechnologie mbH, Duisburg (DE)

( * ) Notice: Subject to any disclaimer, the term of this patent is extended or adjusted under 35 U.S.C. 154(b) by 783 days.

(21) Appl. No.: 10/593,197

(22) PCT Filed: Nov. 17, 2004

(86) PCT No.: PCT/DE2004/002533

§ 371 (c)(1),
(2), (4) Date: Oct. 16, 2006

(87) PCT Pub. No.: WO2005/089944

PCT Pub. Date: Sep. 29, 2005

(65) Prior Publication Data

US 2008/0025888 A1     Jan. 31, 2008

(30) Foreign Application Priority Data

Mar. 17, 2004   (DE) ................... 10 2004 013 161

(51) Int. Cl.
   *B01J 19/00*   (2006.01)
   *B29C 35/08*   (2006.01)

(52) U.S. Cl. .................... 422/68.1; 264/494

(58) Field of Classification Search .............. 422/50, 422/68.1, 99, 100, 129; 264/494
See application file for complete search history.

(56) References Cited

U.S. PATENT DOCUMENTS

| | | |
|---|---|---|
| 5,847,068 A | 12/1998 | Maxein et al. |
| 6,213,151 B1 | 4/2001 | Jacobson et al. |
| 6,623,613 B1 | 9/2003 | Mathies et al. |
| 6,766,817 B2 | 7/2004 | da Silva |
| 6,918,404 B2 | 7/2005 | Dias da Silva |
| 7,066,586 B2 | 6/2006 | da Silva |
| 7,285,255 B2 | 10/2007 | Kadlec et al. |
| 2002/0125612 A1 | 9/2002 | Gotzen et al. |
| 2007/0212281 A1 | 9/2007 | Kadlec et al. |

FOREIGN PATENT DOCUMENTS

| | | |
|---|---|---|
| DE | 44 20 996 | 1/1996 |
| DE | 101 44 579 | 3/2003 |
| DE | 10144579 A1 * | 3/2003 |
| WO | WO 9844072 | 10/1998 |
| WO | WO 0058724 | 10/2000 |

OTHER PUBLICATIONS

Durchbruch in der Biotechnologie, mit RMPD®-microFLUDIK,(Oct. 24, 2000).*
www.microtec-d.com/media/a_homepage/a01_startseite/produkte_biogentechnik.pdf, "RPMD-Systeme fur die Biogentechnik", Oct. 16, 2006.
www16.medica.de/cipp/md_ medica/custom/pub/content,lang,1/oid,11158/ticket.g_u_e_s_t/local_lang,1 AR "Durchbruch in der Biotechnologie, mit RPMD-microFLUIDIK", MEDICA.de News archive Oct. 24, 2000.
Goetzen, R. et al., www.microtec-d.com/media/e_downloads/microtecneu.pdf, "Rapid Micro Product Development RMPD" Jul. 25, 2002.
www.medica.de/cipp/md_medica/custom/pub/content,lang,1/oid,11158/ticket,g_u_e_s_t/local_lang,1, "Durchbruch in der Biotechnologie, mit RMPD®- microFLUIDIK," Oct. 24, 2000, MEDICA.de News Archive, one page. (ISR).

* cited by examiner

*Primary Examiner*—Glenn Caldarola
*Assistant Examiner*—Randy Boyer
(74) *Attorney, Agent, or Firm*—Collard & Roe, P.C.

(57) ABSTRACT

The invention relates to a microfluidic chip for biological, chemical and medical analysis. Cavities and channels, which connect these cavities to one another and which transport, based on the capillary effect, liquids required for carrying out analysis and synthesis, are arranged inside the microfluidic chip. At least one of the cavities is a reaction chamber. The microfluidic chip is characterized by having a layered construction made of light-curing hydrophilic plastic material based on a 3-D layer model and by having a covering layer made of a hydrophobic material. In the layered body made of hydrophilic material, channels that come from different cavities and do not intersect lead to the at least one reaction chamber.

4 Claims, 1 Drawing Sheet

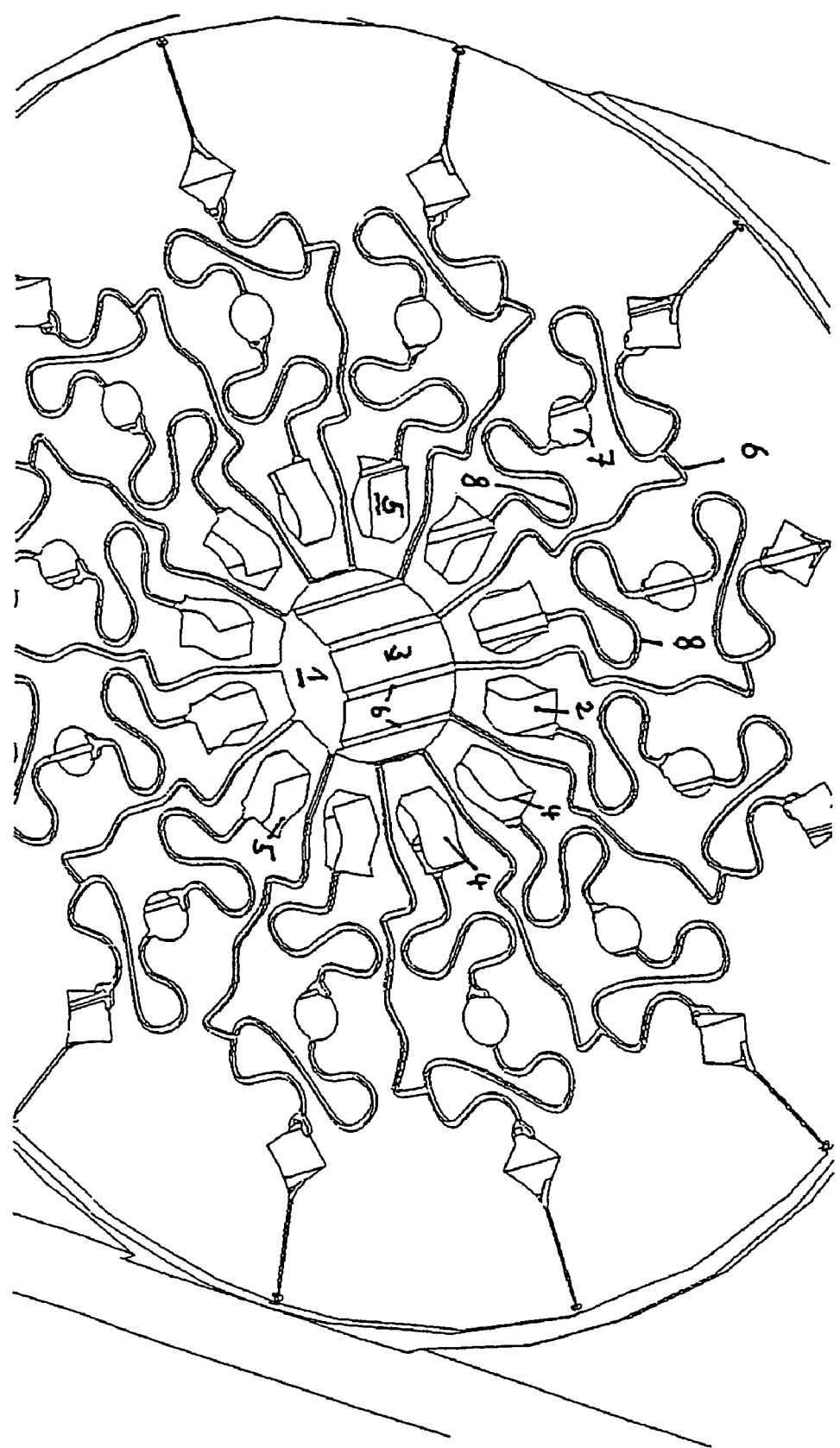

MICROFLUIDIC CHIP

CROSS REFERENCE TO RELATED APPLICATIONS

Applicant claims priority under 35 U.S.C. §119 of German Application No. 10 2004 013 161.9 filed Mar. 17, 2004. Applicant also claims priority under 35 U.S.C. §365 of PCT/DE2004/002533 filed Nov. 17, 2004. The international application under PCT article 21(2) was not published in English.

The invention relates to a microfluidic chip for biological, chemical, and medical analysis and synthesis, in which cavities and channels that connect the former with one another, which channels transport fluids required for the analysis, on the basis of the capillary effect, are disposed, whereby at least one of these cavities is a reaction chamber.

Microfluidic components utilize capillary, hydrophilic, and hydrophobic forces to be able to move fluid substances in a system, without pumps. For this purpose, branchers and mixers are required. However, in the case of the systems that exist today, there is no possibility for allowing two fluid streams to intersect on a fluidic chip, without mixing taking place.

In the case of the chip in question, however, a fluid to be examined (blood) must first be brought together with an analysis fluid in a reaction chamber, in order to be able to make statements concerning the substance to be examined, on the basis of the observed reaction.

The microfluidic chip must therefore be structured in such a manner that the channels that transport the fluid, as well as the cavities from which the fluids are transported, are completely separated from one another.

This is possible in simple manner, if the chip can be produced in a manner that also allows undercuts.

Therefore the invention accomplishes the task underlying it by means of a layered construction of light-curing hydrophilic plastic material, on the basis of a 3D layer model, and a cover layer made of a hydrophobic material, whereby channels that come out of different cavities, and run without intersections in the layer body structured from hydrophilic material empty into the at least one reaction chamber.

This layered construction is a known generative technology in which a light-curing fluid is held between two plates because of its surface tension, for example. One of these plates is permeable for electromagnetic waves. The method is described in DE-PS 44 20 996.

The model of the body to be produced is stored in a computer, for example, also in virtual layers, which are called up, one after the other, and extremely thin layers can be produced by means of moving the two plates apart, layer by layer, and allowing fresh material to flow in; these layers make it possible to produce extremely precise and extremely small structures, such as the cavities, the channels, as well as cavities that are partially bridged by crosspieces, for example. In this manner, it is possible, for one thing, for the cavities to be strictly separated from one another, and, for another thing, for the channels that transport the different fluids to also be separated.

In a preferred embodiment of the invention, it is provided that a central cavity covered by the hydrophobic layer is generated in the chip, which cavity is surrounded by a cavity configured in ring shape, which also has openings covered by the hydrophobic layer, separated from one another by means of crosspieces, from which openings one channel, in each instance, leads to a reaction chamber assigned to the opening, which reaction chamber is disposed around the central cavity and around the ring-shaped cavity, with other reaction chambers, in star shape, while channels that are placed in the surface of the crosspieces, bridging the ring cavity, lead from the central cavity to the assigned reaction chamber, in each instance, whereby the channels that proceed from the ring cavity as well as from the central cavity make a transition into grooves that are open towards the interior of the cavities and rise in the walls of the cavities, in perpendicular manner.

In this connection, the method of generative, i.e. layered construction that is used offers the guarantee that the edges of the channels can be made extremely precise at the locations where they make a transition from the horizontal to the vertical, so that the capillary effect is very marked in the case of the hydrophilic material.

According to another exemplary embodiment of the invention, it is provided that the channels that are disposed vertically in the walls form an acute angle with the bottom surface at their cavity-bottom-side end.

This means that at this location, the channel that runs vertically downward steps back a short piece out of the cavity, an embodiment that is also not possible by means of normal shaping technology. However, such a configuration is essentially for optimization of the capillary effect.

For further optimization of the capillary effect, it is desirable for the channels and cavities, respectively, to be covered by a hydrophobic layer.

This hydrophobic layer is produced, according to claim 4, in such a manner that first, a film of one or more layers of light-curing plastic material is generated, whereby the final layer is only partially polymerized. The polymerization takes place in known manner, by means of exposure with electromagnetic waves.

The film produced in this manner is laid onto the microfluidic chip generated previously, with the partially polymerized layer, and then the layer that was only partially polymerized up to that time is polymerized through, so that the chip is given a monolithic structure.

In this manner, it is possible to do without adhesives, etc., which could fill up the fine channels when applying the cover.

In order to be able to produce large numbers of the microfluidic chip in question, claim 5 provides that the film is continuously produced between at least one pair of rollers, whereby the light-curing material is disposed between the two rollers, one of which has the exposure device that serves for curing, and the cover layer produced in this manner is laid onto the microfluidic chips that are produced in large numbers, and polymerized through, also using a continuous method.

In the attached drawing, a microfluidic chip is shown in a detail and in a greatly enlarged representation, but the cover layer has been left out.

The chip has a central cavity 1, which is surrounded by a ring-shaped cavity 2 and separated from the latter by the wall 3. The ring-shaped cavity 2 has openings 4 disposed in star shape, which are separated from one another by crosspieces 5.

Channels 6 rise from the bottom of the central cavity 1, in vertical manner, which channels are guided up to a further cavity 7 by way of the crosspieces 5. The cavity 7 is a reaction chamber, for example.

In this chamber, a fluid that has been passed in from the central cavity 1 by way of the channels 6 reacts with an analysis fluid, for example, which is passed in from the ring-shaped cavity 2 by way of channels 8. The channel 8 rises upward from the bottom of the ring-shaped cavity 2, in the wall of this cavity, and is then passed to the cavity 7 by the channel 6, without any intersection.

The transport of the fluids comes about by means of the capillary effect of the hydrophilic material of which the microfluidic chip consists. In this connection, it is essential, for one thing, that the cover material, not shown, is configured to be hydrophobic, and, for another thing, that the edges of the channels are configured to be extremely precise at the locations of the transition from the vertical to the horizontal. This relates, for one thing, to the edges at which the vertically rising channels 6 and 8 lead out of the cavities 1 and 2, in each instance, to the chip surface, and to the edges at which these vertically rising channels meet the bottom of the cavity, in each instance. At these locations, the channels are guided back into the wall a piece, and form an acute angle with the bottom surface here.

Such chips are filled with an analysis fluid, for example, in the ring space 2, by the manufacturer. For an examination, the material to be examined, for example blood or components of blood, is filled into the central cavity 1 by means of a pipette or syringe, through the cover layer not shown here. On the basis of the capillary forces, the two fluids then get into the chamber 7. Statements about the substance to be examined can be made on the basis of the reaction that takes place there.

The invention claimed is:

1. A microfluidic chip for biological, chemical, and medical analysis, in which cavities and channels that connect the former with one another, which channels transport fluids required for the analysis, on the basis of the capillary effect, are disposed, whereby at least one of these cavities is a reaction chamber comprising a layered construction of light-curing hydrophilic plastic material, on the basis of a 3D layer model, and a cover layer made of a hydrophobic material, whereby channels that come out of different cavities, and run without intersections in the layer body structured from hydrophilic material empty into the at least one reaction chamber, wherein a central cavity covered by the hydrophobic layer is generated in the chip, which cavity is surrounded by a ring cavity configured in ring shape, which also has openings covered by the hydrophobic layer, separated from one another by means of crosspieces, from which openings one channel, in each instance, leads to a reaction chamber assigned to the opening, which reaction chamber is disposed around the central cavity and around the ring cavity, with other reaction chambers, in star shape, while channels that are placed in the surface of the crosspieces, bridging the ring cavity, lead from the central cavity to the assigned reaction chamber, in each instance, whereby the channels that proceed from the ring cavity as well as from the central cavity make a transition into grooves that are open towards the interior of the cavities and rise in the walls of the cavities, in perpendicular manner.

2. The microfluidic chip according to claim 1, wherein the channels that are disposed vertically in the walls form an acute angle with the bottom surface at their cavity-bottom-side end.

3. A method for producing a cover layer for a microfluidic chip comprising the steps of:
   (a) generating a microfluidic chip for biological, chemical, and medical analysis, in which cavities and channels that connect the former with one another, which channels transport fluids required for the analysis, on the basis of the capillary effect, are disposed, whereby at least one of these cavities is a reaction chamber comprising a layered construction of light-curing hydrophilic plastic material, on the basis of a 3D layer model, and a cover layer made of a hydrophobic material, whereby channels that come out of different cavities, and run without intersections in the layer body structured from hydrophilic material empty into the at least one reaction chamber, wherein a central cavity covered by the hydrophobic layer is generated in the chip, which cavity is surrounded by a ring cavity configured in ring shape, which also has openings covered by the hydrophobic layer, separated from one another by means of crosspieces, from which openings one channel, in each instance, leads to a reaction chamber assigned to the opening, which reaction chamber is disposed around the central cavity and around the ring cavity, with other reaction chambers, in star shape, while channels that are placed in the surface of the crosspieces, bridging the ring cavity, lead from the central cavity to the assigned reaction chamber, in each instance, whereby the channels that proceed from the ring cavity as well as from the central cavity make a transition into grooves that are open towards the interior of the cavities and rise in the walls of the cavities, in perpendicular manner; and
   (b) generating a film of one or more layers of light-curing plastic material, whereby the final layer is only partially polymerized, after which the film formed in this manner is laid onto the microfluidic chip generated previously, with the partially polyrmerized layer, and the layer that was only partially polyrmerized up to that time is polyrmerized through, so that the chip is given a monolithic structure.

4. The method according to claim 3, wherein the film is continuously produced between at least one pair of rollers, whereby the light-curing material is disposed between the two rollers, one of which has the exposure device that serves for curing, and the cover layer produced in this manner is laid onto the microfluidic chips that are produced in large numbers, and polymerized through, also using a continuous method.

* * * * *